(12) United States Patent
Abell et al.

(10) Patent No.: US 6,451,570 B1
(45) Date of Patent: Sep. 17, 2002

(54) MUTANTS OF MONOAMINE OXIDASE B

(75) Inventors: Creed W. Abell, Austin; Duane A. Lewis, Big Spring, both of TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/265,653

(22) Filed: Mar. 10, 1999

Related U.S. Application Data

(60) Provisional application No. 60/077,482, filed on Mar. 11, 1998.

(51) Int. Cl.[7] .......................... C12N 9/06; C12N 15/63; C12N 15/53
(52) U.S. Cl. .................... 435/191; 435/189; 435/320.1; 530/350; 536/23.5
(58) Field of Search .................. 530/350; 536/23.5; 435/320.1, 189, 191

*Primary Examiner*—Gary L. Kunz
*Assistant Examiner*—Stephen Gucker
(74) *Attorney, Agent, or Firm*—Benjamin Aaron Adler

(57) ABSTRACT

A highly conserved active site helix present within the P-450 superfamily of proteins is found also in monoamine oxidase (MAO) B, a major enzyme that catalyzes deamination of neuro- and vaso-active amines in the nervous system of mammals. Mutation within the conserved region of the MAO B enzyme directly reduces MAO B's activity and alters its pH profile, which allows for indirect regulation of the cellular neurotransmitters and vasoamines.

4 Claims, 4 Drawing Sheets

(1 of 4 Drawing Sheet(s) Filed in Color)

| Protein | | | | | | | | | | | | | | | |
|---|---|---|---|---|---|---|---|---|---|---|---|---|---|---|---|
| Human MAO B | D | R | I | Y | F | A | G | T | E | T | A | T | H | W | S | G | Y-435 | SEQ ID No. 1 |
| Human MAO A | G | R | H | F | F | A | G | T | E | T | A | T | K | W | S | G | Y-444 | SEQ ID No. 14 |
| Rat MAO B | G | K | I | F | F | A | G | T | E | T | A | S | H | W | S | G | Y-435 | SEQ ID No. 15 |
| Rat MAO A | G | R | H | Y | F | A | G | T | E | T | A | T | Q | W | S | G | Y-444 | SEQ ID No. 16 |
| Bovine MAO A | G | R | H | F | F | A | G | T | E | T | A | T | Q | W | S | G | Y-444 | SEQ ID No. 17 |
| P. Putida P-450cam | G | L | L | L | V | G | G | L | D | T | V | V | N | F | L | S | P-259 | SEQ ID No. 18 |
| Pseud. P-450terp | V | A | H | A | T | A | G | H | H | T | T | S | S | S | S | G | G-278 | SEQ ID No. 19 |
| B. Megat. P-450BM-3 | I | T | F | L | I | A | G | H | E | T | T | S | G | L | L | S | F-275 | SEQ ID No. 20 |
| Rabbit P-450LM2 | L | S | L | F | F | A | G | T | E | T | T | S | T | T | L | R | Y-309 | SEQ ID No. 21 |
| Rat P-450PCN2 | V | H | F | H | F | A | G | Y | E | T | T | S | S | T | L | S | F-317 | SEQ ID No. 22 |
| Rat P-450b | L | L | L | F | F | G | A | G | F | E | T | V | T | T | T | L | R | Y-309 | SEQ ID No. 23 |
| Rat P-450c | F | D | L | F | G | A | G | F | D | T | T | I | T | A | I | S | W-332 | SEQ ID No. 24 |
| Rat P-450d | N | D | H | F | G | A | G | F | E | T | T | V | T | A | H | F | W-326 | SEQ ID No. 25 |
| Rabbit P-450ω-1 | S | D | V | F | M | A | A | G | T | E | T | T | S | T | T | L | R | Y-308 | SEQ ID No. 26 |
| Rabbit P-450α | T | D | V | F | A | A | G | T | E | T | T | S | T | T | L | R | Y-308 | SEQ ID No. 27 |

Fig. 1

SEQUENCE LISTING

```
<160> NUMBER OF SEQ ID NOS: 27

<210> SEQ ID NO 1
<211> LENGTH: 17
<212> TYPE: PRT
<213> ORGANISM: Homo sapiens
<220> FEATURE:
<223> OTHER INFORMATION: Amino acid sequence of  active site of wild type
      MAO B enzyme

<400> SEQUENCE: 1

Asp Arg Ile Tyr Phe Ala Gly Thr Glu Thr A la Thr His Trp Ser
                5                   10                  15

Gly Tyr

<210> SEQ ID NO 2
<211> LENGTH: 11
<212> TYPE: PRT
<213> ORGANISM: Artificial sequence
<220> FEATURE:
<223> OTHER INFORMATION: Amino acid sequence of  F423A mutant cDNA

<400> SEQUENCE: 2

Asp Arg Ile Tyr Ala Ala Gly Thr Glu Thr A la
                5                   10

<210> SEQ ID NO 3
```

```
<211> LENGTH: 14
<212> TYPE: PRT
<213> ORGANISM: Artificial sequence
<220> FEATURE:
<223> OTHER INFORMATION: Amino acid sequence of E427Q mutant cDNA

<400> SEQUENCE: 3

Arg Ile Tyr Phe Ala Gly Thr Gln Thr Ala T hr His Trp Ser
                5                   10

<210> SEQ ID NO 4
<211> LENGTH: 14
<212> TYPE: PRT
<213> ORGANISM: Artificial sequence
<220> FEATURE:
<223> OTHER INFORMATION: Amino acid sequence of T428A mutant cDNA

<400> SEQUENCE: 4

Arg Ile Tyr Phe Ala Gly Thr Glu Ala Ala T hr His Trp Ser
                5                   10

<210> SEQ ID NO 5
<211> LENGTH: 14
<212> TYPE: PRT
<213> ORGANISM: Artificial sequence
<220> FEATURE:
<223> OTHER INFORMATION: Amino acid sequence of T428S mutant cDNA

<400> SEQUENCE: 5

Arg Ile Tyr Phe Ala Gly Thr Glu Ser Ala T hr His Trp Ser
                5                   10

<210> SEQ ID NO 6
<211> LENGTH: 11
<212> TYPE: PRT
<213> ORGANISM: Homo sapiens
<220> FEATURE:
<223> OTHER INFORMATION: Amino acid sequence of active site of wild type
      MAO B encoded by cDNA

<400> SEQUENCE: 6

Asp Arg Ile Tyr Phe Ala Gly Thr Glu Thr A la
                5                   10

<210> SEQ ID NO 7
<211> LENGTH: 33
<212> TYPE: DNA
<213> ORGANISM: Artificial sequence
<220> FEATURE:
<223> OTHER INFORMATION: Nucleotide sequence of primer used to construct
      wild type MAO B cDNA

<400> SEQUENCE: 7
ggacaggatt tactttgcag gcaccgagac tgc                                33

<210> SEQ ID NO 8
<211> LENGTH: 33
<212> TYPE: DNA
<213> ORGANISM: artificial sequence
<220> FEATURE:
<223> OTHER INFORMATION: Nucleotide sequence of mutagenic primer used to
      construct F423A cDNA

<400> SEQUENCE: 8
ggacaggatt tacgctgccg gcaccgagac tgc                                33

<210> SEQ ID NO 9
```

```
<211> LENGTH: 14
<212> TYPE: PRT
<213> ORGANISM: Homo sapiens
<220> FEATURE:
<223> OTHER INFORMATION: Amino acid sequence of  active site of wild type
      MAO B encoded by cDNA

<400> SEQUENCE: 9

Arg Ile Tyr Phe Ala Gly Thr Glu Thr Ala T hr His Trp Ser
                5                   10

<210> SEQ ID NO 10
<211> LENGTH: 40
<212> TYPE: DNA
<213> ORGANISM: artificial sequence
<220> FEATURE:
<223> OTHER INFORMATION: Nucleotide sequence of primer used to construct
      wild type MAO B cDNA

<400> SEQUENCE: 10
ggatttactt tgcaggcacc gagactgcca cacactggag                              40

<210> SEQ ID NO 11
<211> LENGTH: 40
<212> TYPE: DNA
<213> ORGANISM: artificial sequence
<220> FEATURE:
<223> OTHER INFORMATION: Nucleotide sequence of mutagenic primer used to
      construct E427Q cDNA

<400> SEQUENCE: 11
ggatttactt tgccggcacc cagactgcta cacactggag                              40

<210> SEQ ID NO 12
<211> LENGTH: 40
<212> TYPE: DNA
<213> ORGANISM: artificial sequence
<220> FEATURE:
<223> OTHER INFORMATION: Nucleotide sequence of mutagenic primer used to
      construct T428A cDNA

<400> SEQUENCE: 12
ggatttactt tgccggcacc gaggctgcta cacactggag                              40

<210> SEQ ID NO 13
<211> LENGTH: 40
<212> TYPE: DNA
<213> ORGANISM: artificial sequence
<220> FEATURE:
<223> OTHER INFORMATION: Nucleotide sequence of mutagenic primer used to
      construct T428S cDNA

<400> SEQUENCE: 13
ggatttactt tgccggcacc gagtctgcta cacactggag                              40

<210> SEQ ID NO 14
<211> LENGTH: 17
<212> TYPE: PRT
<213> ORGANISM: Homo sapiens
<220> FEATURE:
<223> OTHER INFORMATION: Amino acid sequence of  active site of wild type
      MAO A enzyme

<400> SEQUENCE: 14

Gly Arg Ile Phe Phe Ala Gly Thr Glu Thr A la Thr Lys Trp Ser
                5                   10                  15

Gly Tyr
```

```
<210> SEQ ID NO 15
<211> LENGTH: 17
<212> TYPE: PRT
<213> ORGANISM: Rat sp.
<220> FEATURE:
<223> OTHER INFORMATION: Amino acid sequence of active site of rat
      MAO B enzyme

<400> SEQUENCE: 15

Gly Lys Ile Phe Phe Ala Gly Thr Glu Thr Ala Ser His Trp Ser
                 5                  10                  15

Gly Tyr

<210> SEQ ID NO 16
<211> LENGTH: 17
<212> TYPE: PRT
<213> ORGANISM: Rat sp.
<220> FEATURE:
<223> OTHER INFORMATION: Amino acid sequence of active site of rat
      MAO A enzyme

<400> SEQUENCE: 16

Gly Arg Ile Tyr Phe Ala Gly Thr Glu Thr Ala Thr Glu Trp Ser
                 5                  10                  15

Gly Tyr

<210> SEQ ID NO 17
<211> LENGTH: 17
<212> TYPE: PRT
<213> ORGANISM: Bovine sp.
<220> FEATURE:
<223> OTHER INFORMATION: Amino acid sequence of active site of bovine
      MAO A enzyme

<400> SEQUENCE: 17

Gly Arg Ile Tyr Phe Ala Gly Thr Glu Thr Ala Thr Glu Trp Ser
                 5                  10                  15

Gly Tyr

<210> SEQ ID NO 18
<211> LENGTH: 17
<212> TYPE: PRT
<213> ORGANISM: P. putida
<220> FEATURE:
<223> OTHER INFORMATION: Amino acid sequence co ntaining conserved site
      of P.putida P-450cam

<400> SEQUENCE: 18

Gly Leu Leu Leu Val Gly Gly Leu Asp Thr Val Val Asn Phe Leu
                 5                  10                  15

Ser Pro

<210> SEQ ID NO 19
<211> LENGTH: 17
<212> TYPE: PRT
<213> ORGANISM: Pseudomonas sp.
<220> FEATURE:
<223> OTHER INFORMATION: Amino acid sequence co ntaining conserved site
      of Pseudomonas P-450terp

<400> SEQUENCE: 19

Val Ala Ile Ala Thr Ala Gly His Asp Thr Thr Ser Ser Ser Ser
                 5                  10                  15
```

Gly Gly

<210> SEQ ID NO 20
<211> LENGTH: 17
<212> TYPE: PRT
<213> ORGANISM: Bacillus megaterium
<220> FEATURE:
<223> OTHER INFORMATION: Amino acid sequence co ntaining conserved site
      of Bacillus megaterium P-450BM3

<400> SEQUENCE: 20

Ile Thr Phe Leu Ile Ala Gly His Glu Thr T hr Ser Gly Leu Leu
                5                   10                  15

Ser Phe

<210> SEQ ID NO 21
<211> LENGTH: 17
<212> TYPE: PRT
<213> ORGANISM: Lepus sp.
<220> FEATURE:
<223> OTHER INFORMATION: Amino acid sequence co ntaining conserved site
      of Rabbit P-450LM2

<400> SEQUENCE: 21

Leu Ser Leu Phe Phe Ala Gly Thr Glu Thr T hr Ser Thr Thr Leu
                5                   10                  15

Arg Tyr

<210> SEQ ID NO 22
<211> LENGTH: 17
<212> TYPE: PRT
<213> ORGANISM: Rat sp.
<220> FEATURE:
<223> OTHER INFORMATION: Amino acid sequence co ntaining conserved site
      of Rat P-450PCN2

<400> SEQUENCE: 22

Val Ile Phe Ile Phe Ala Gly Tyr Glu Thr T hr Ser Ser Thr Leu
                5                   10                  15

Ser Phe

<210> SEQ ID NO 23
<211> LENGTH: 17
<212> TYPE: PRT
<213> ORGANISM: Rat sp.
<220> FEATURE:
<223> OTHER INFORMATION: Amino acid sequence co ntaining conserved site
      of Rat P-450b

<400> SEQUENCE: 23

Leu Ser Leu Phe Phe Ala Gly Thr Glu Thr S er Ser Thr Thr Leu
                5                   10                  15

Arg Tyr

<210> SEQ ID NO 24
<211> LENGTH: 17
<212> TYPE: PRT
<213> ORGANISM: Rat sp.
<220> FEATURE:
<223> OTHER INFORMATION: Amino acid sequence co ntaining conserved site
      of Rat P-450c

<400> SEQUENCE: 24

Phe Asp Leu Phe Gly Ala Gly Phe Asp Thr I le Thr Thr Ala Ile
                5                   10                  15

```
Ser Trp

<210> SEQ ID NO 25
<211> LENGTH: 17
<212> TYPE: PRT
<213> ORGANISM: Rat sp.
<220> FEATURE:
<223> OTHER INFORMATION: Amino acid sequence co ntaining conserved site
      of Rat P-450d

<400> SEQUENCE: 25

Asn Asp Ile Phe Gly Ala Gly Phe Glu Thr V al Thr Thr Ala Ile
                5                   10                  15

Phe Trp

<210> SEQ ID NO 26
<211> LENGTH: 17
<212> TYPE: PRT
<213> ORGANISM: Rat sp.
<220> FEATURE:
<223> OTHER INFORMATION: Amino acid sequence co ntaining conserved site
      of Rat P-450ω-1

<400> SEQUENCE: 26

Ser Asp Val Phe Met Ala Gly Thr Glu Thr T hr Ser Thr Thr Leu
                5                   10                  15

Arg Tyr

<210> SEQ ID NO 27
<211> LENGTH: 17
<212> TYPE: PRT
<213> ORGANISM: Rat sp.
<220> FEATURE:
<223> OTHER INFORMATION: Amino acid sequence co ntaining conserved site
      of Rat P-450α

<400> SEQUENCE: 27

Thr Asp Val Phe Ala Ala Gly Thr Glu Thr T hr Ser Thr Thr Leu
                5                   10                  15

Arg Tyr
```

MUTANTS OF MONOAMINE OXIDASE B

CROSS-REFERENCE TO RELATED APPLICATION

This application claims benefit of provisional application Serial No. 60/077,482, filed Mar. 11, 1,998, now abandoned.

FEDERAL FUNDING LEGEND

This invention was produced in part using funds obtained through the National Institutes of Health research grant NS24932 and training grant AA07471. Consequently, the federal government has certain rights in this invention.

BACKGROUND OF THE INVENTION

1. Field of the Invention

The present invention relates generally to neurobiology. More specifically, the present invention relates to molecular engineering of monoamine oxidases to determine those domains that play a role in the regulation of cellular neurotransmitters and vasoamines.

2. Description of the Related Art

The cytochrome P-450 superfamily of hemoproteins are extremely diverse in amino acid sequence, intron/exon organization, cellular localization, host organisms, substrates, and metabolic oxidation and reduction reactions. Common elements of the P-450s include a Soret absorption band at 450 nm associated with a n obligatory heme cofactor, and conserved structural elements surrounding the heme in the active site. The α-helix which traverses the active site of P-450cam and P-450BM-3 is also predicted in the primary and secondary structure of 52 species of membrane bound P-450 (16, 25). Although P-450BM-3 contains only 16% sequence identity to P-450cam and differs significantly from P-450cam in tertiary structure, redox partner preferences and substrate specificities, a region of high sequence homology is retained. In these P-450 enzymes, this conserved sequence resides within an extended α-helix which traverses the active site.

Since this sequence is an integral part of the active site in P-450 enzymes, site-directed mutagenesis studies have been undertaken in numerous laboratories to identify specific residues that play a role in the active site (16). Although the specific role of several amino acid residues in this region are still being investigated, the residues which correspond to Asp251 and Thr252 of P-450cam are widely accepted as crucial for the activity of P-450 enzymes (17). For example, mutagenesis of those residues in P-450cam, P-450d or aromatase resulted in a dramatic decrease in activities (18). Furthermore, Gerber and Sligar (18) observed a significant change in the pH profile of P-450cam when Asp251 was changed to Asn (from parabolic to descending slope). They proposed a model in which the Asp251 and Thr252 residues of P-450cam provide a proton relay to protonate the heme-bound dioxygen prior to O—O bond scission and water release.

The Asp251 residue of P-450cam has also been reported to play a role in substrate entry (20). Although a depression is observed at the surface of the protein that likely serves as the access channel for the substrate, the entry is blocked by the presence of a salt bridge (12). Deprez et al. (20) suggest that the salt bridge could control the opening of the structure. Specifically, Arg186, Lys178 (residues in P-450cam which reside outside of the active site α-helix), and Asp251 were hypothesized to control substrate diffusion to the active site. Deprez et al. analyzed a D251N mutant enzyme by determining the effect of alteration of the ionic strength and dielectric constant of the medium on the substrate binding step. Substrate access was highly dependent on electrostatic interactions in the wild-type enzyme, but to a much lesser extent in the D251N mutant. Based upon these findings and the crystal structure resolved by Poulos et al. (12), Deprez et al. concluded that Asp-251 participates in a bifurcated salt bridge and plays a role in regulation of substrate diffusion to the active site.

Residue Thr252 of P-450cam is the most widely studied residue in this and other P-450 enzymes. Examination of the crystal structures of P-450cam suggested that Thr252 forms a hydrogen bond with the carbonyl oxygen of the conserved Gly248, causing an atypical kink in the helix to form the $O_2$ binding pocket (21). However, this putative role for Thr252 was later eliminated when a mutant enzyme (T252A), which is incapable of hydrogen bonding with Gly248, was found to retain the same characteristic kink in the $O_2$ binding pocket (22). Other studies support the conclusion that this conserved Thr of the cytochrome P-450 enzymes plays a role in substrate binding and specificity (23).

Monoamine oxidase A and B (MAO A and MAO B) are the major enzymes that catalyze the oxidative deamination of neuroactive and vasoactive amines in the central nervous system and peripheral tissues of mammals. These flavoenzymes are located in the outer mitochondrial membrane and are very similar i n deduced amino acid sequence (1) and gene organization (2). MAO A and B can be distinguished by differences in substrate preference and inhibitor specificity (3), tissue and cell distribution (4), and immunological properties (5).

Since. the structure of MAO A or B has not been determined, attempts to identify active site domains have focused on substrate/inhibitor binding studies (6), symmetry modeling (7), FTIR spectroscopy (8), site-directed mutagenesis studies (9), analysis of MAO A/B chimeras (10), and expression of truncated polypeptides (11). Collectively, these studies provided increased insight into the functional regions of these enzymes, but the active site domain(s) and the specific residues that participate in the oxidative deamination of substrates have not been identified. Powell et al. (1), however, determined the amino acid sequence of bovine MAO A, and identified a short segment that exhibited high sequence identity to a region in cytochrome P-450 in rat.

The prior art is deficient in indentifying the active site of the monoamine oxidase (MAO) B enzyme and the effect that mutations to this site have on enzyme activity and the regulation of neuro- and vaso-amines. The present invention fulfills this long-standing need and desire in the art.

SUMMARY OF THE INVENTION

Monoamine oxidases A and B (MAO A and B) are the major enzymes in mammals that catalyze the oxidative deamination of neurotransmitters and peripheral vasoactive amines. Although these enzymes are among the most widely studied flavoproteins, their integral association with the outer mitochondrial membrane has precluded elucidation of their three-dimensional structure and identification of the active site domain(s). By comparing the primary sequence of MAO B to selected proteins of known structure, three amino acids (Phe423, Glu427, and Thr428) have been identified that constitute critical residues within the active site. The region in MAO B that contains these residues exhibits high sequence identity to a central active site helix in the cytochrome P-450 superfamily. Furthermore, this region, referred to herein as the conserved sequence, is predicted to have the same secondary structure as P-450cam and displays striking similarities in site-directed mutagenesis studies.

One object of the present invention is to provide isolated, genetically-engineered MAO B enzymes having at least one amino acid substitution for amino acids in the wildtype MAO B active site, where the wildtype amino acid is Phenylalanine at position 423, Glutamate at position 427 and Threonine at position 428. The present invention additionally provides isolated DNAs that encode these genetically-engineered MAO B enzymes, and plasmids containing these DNAs along with regulatory elements necessary for expression of these DNAs in a cell.

Specific embodiments of this object of the present invention include where the wildtype amino acid is Phenylalanine 423, the amino acid substitution is Alanine; where the wildtype amino acid is Glutamate 427, the amino acid substitution is Glutamine; and where the wildtype amino acid is Threonine 428, the amino acid substitution is Serine or Alanine.

An additional object of the present invention is to provide pharmaceutical compositions which interact with the active site of MAO B. Specific compositions include derivatives of active site components, such as FAD, 2'-deoxy FAD and 3'-deoxy FAD, and derivatives of mechanism-based inhibitors that belong to the acetylenic and cyclopropyl amine classes.

Additionally, an object of the present invention is to provide a method for regulating MAO B comprising the step of mutating an amino acid in the MAO B active site. Specifically, the amino acid to be mutated is selected from the wildtype amino acids Phe 423, Glu 427 and Thr 428.

Another object of the present invention is to provide a description of the active site of monoamine oxidase B, such that pharmaceutical compositions can be designed to interact with the active site. Specific embodiments of this object of the invention include 2'-deoxy FAD, 3'-deoxy FAD, and derivatives of deprenyl (phenylisopropyl-methylproinylamine) and trans-phenylcyclopropylamine. Molecular modeling is applied to determine which derivatives are most likely to interact with components in the active site of the enzyme.

Other and further aspects, features, and advantages of the present invention will be apparent from the following description of the presently preferred embodiments. These embodiments are given for the purpose of disclosure.

BRIEF DESCRIPTION OF THE DRAWINGS

The patent or application file contains at least one drawing executed in color. Copies of this patent or patent application publication and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be, noted, however, that the appended drawings illustrate preferred embodiments of the invention and therefore are not to be considered limiting in their scope.

FIG. 1 shows the amino acid comparison of monoamine oxidase enzymes to an active site region of cytochrome P-450 enzymes. The region of highest sequence identity, the conserved sequence enclosed in the box, is in close proximity to the substrate within an extended α-helix in the P-450 enzymes with known structures. P-450 sequences were adapted from Omura et al. (16). Monoamine oxidase sequences were obtained as noted in (1).

DETAILED DESCRIPTION OF THE INVENTION

Figure 2:
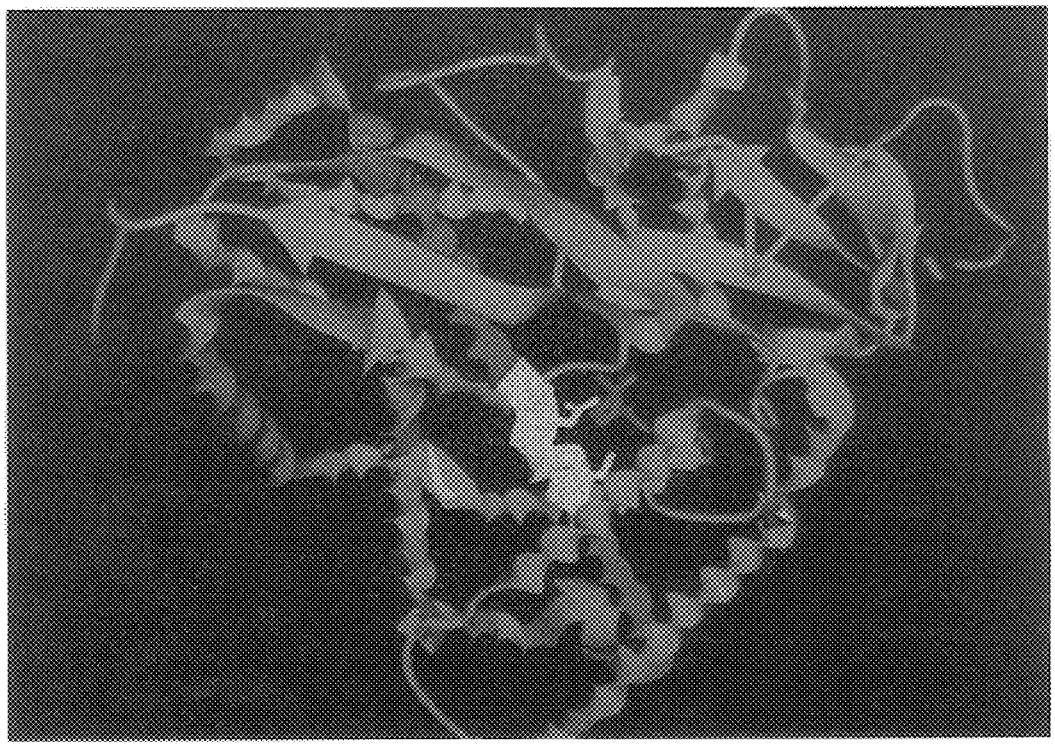
FIG. 2 shows the crystal structure of cytochrome P-450cam (12) using the PDB file coordinates of P-450cam plus camphor by Poulos et al. (12) (heme and water molecules not shown). The conserved sequence identity (depicted in the boxed region of FIG. 1) is shown in yellow within the extended α-helix in cyano. Amino acid residues projecting out of the helix in close proximity to the camphor substrate correspond to residues Val247, Asp251 and Thr252 (from top to bottom) in P-450cam. Thr252 projects away from the viewer. Site-directed mutagenesis was carried out for MAO B at the three residues which align to those shown here (Phe423, Glu427 and Thr428, respectively).

The present invention is directed toward the amino acid sequence and tertiary structure corresponding to the active site for the monoamine oxidase (MAO) B enzyme and the engineering thereof to achieve neurotransmitter regulation.

As used herein, the terms "Monoamine oxidase" or "MAO" refer to the enzyme responsible for the oxidative deamination, and hence deactivation, of the monoamine neurotransmitters 5-hydroxytryptamine (5HT, serotonin), noradrenaline, and dopamine. MAO also has a role in providing protection from other exogenous (i.e., dietary or environmental) amines that might otherwise have adverse effects on, for example, cardiovascular or neuronal function. MAO exists in two main forms, types A and B; MAO-A (specific inhibitor clorgyline) is responsible for the oxidative removal of 5HT and noradrenaline, whereas in humans, MAO-B (specific inhibitor deprenyl) is the enzyme by which dopamine is mainly metabolized. Both forms of MAO are encoded by separate genes on the X chromosome. MAO-B has been been shown to activate a protoxin, MPTP, that produces a Parkinsons-like disorder in humans.

As used herein, the term "cytochrome P450" is a collective term for an extensive family of heme-containing electron-transport molecules present in liver microsomes and involved in enzymatic oxidation of a wide range of substrates and their conversion to forms that are more easily excreted. In some cases, the metabolites produced may be carcinogenic. Cytochromes P450 are also involved in the synthesis of compounds such as steroid hormones and prostaglandins. Many of the 200 or so genes that comprise this family are inducible by various exogenous agents. The inducibility shows genetic variability.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment. A vector is said to be "pharmacologically acceptable" if its administration can be tolerated by a recipient mammal.

A "DNA molecule" refers to the polymeric form of deoxyribonucleotides (adenine, guanine, thymine, or cytosine) in either single stranded form, or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a complementary sequence to the mRNA).

A DNA "coding sequence" is a double-stranded DNA sequence which is transcribed into RNA and translated into a polypeptide in vivo when placed under the control of appropriate regulatory sequences. The boundaries of the coding sequence are determined by a start codon at the 5' (amino) terminus and a translational stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined b y mapping with nuclease S1), as well as protein binding domains (consensus sequences) responsible for the binding of RNA polymerase. Eukaryotic promoters will often, but not always, contain "TATA" boxes and "CAT" boxes. Various promoters may be used to drive vectors.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "selection gene" refers to a gene that enables the discrimination of cells displaying a required phenotype upon implementation of certain conditions. For example, the growth of bacteria in medium containing antibiotics to select for the bacterial cells containing antibiotic resistance genes.

The term "oligonucleotide" or "probe" as used herein, refers to a molecule comprised of ribonucleotides or deoxyribonucleotides. The exact size of the oligonucleotide or probe will depend upon many factors which, in turn, depend upon the ultimate function and use of the oligonucleotide.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiments under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, a coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

Transcriptional and translational control sequences are DNA regulatory sequences, such as promoters, enhancers, polyadenylation signals, terminators, and the like, that provide for the expression of a coding sequence in a host cell.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomeclature, J Biol. Chem., 243:3552–59 (1969), abbreviations for amino acid residues are shown in the following Table of Correspondence:

TABLE OF CORRESPONDENCE

| 1-Letter | 3-Letter | AMINO ACID |
| --- | --- | --- |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| W | Trp | Tryptophan |
| R | Arg | Arginine |
| D | Asp | Aspartic acid |
| N | Asn | Asparagine |
| C | Cys | Cysteine |

It should be noted that all amino acid sequences are represented herein by formulae whose left and right orientation is in the conventional direction of amino-terminus to carboxy-terminus. Furthermore, it should be noted that a dash at the beginning or end of an amino acid sequence indicates a peptide bond to a further sequence of one or more amino-acid residues. The above Table is presented to correlate the three-letter and one-letter notations which may appear alternately herein.

The present invention is directed towards an isolated, genetically-engineered cellular MAO B enzyme having at least one amino acid substitution for a wildtype amino acid in a MAO B active site, where the wildtype amino acid is selected from the group of Phe423, Glu427 and Thr428. The present invention also provides for an isolated DNA encoding the isolated, genetically-engineered MAO B enzyme. Furthermore, the present invention provides for a plasmid containing the DNA encoding the isolated, genetically-engineered MAO B enzyme and regulatory elements necessary for expression.

The present invention is specifically directed towards an isolated, genetically-engineered cellular MAO B enzyme, in which the wildtype amino acid, Phe423, has been substituted with Alanine. The present invention is also specifically directed towards an isolated, genetically-engineered cellular MAO B enzyme, in which the wildtype amino acid, Glu427, has been substituted with Glutamine. The present invention is also specifically directed towards an isolated, genetically-engineered cellular MAO B enzyme, in which the wildtype amino acid, Thr428, has been substituted with either Serine or Alanine.

The present invention is also directed towards a pharmaceutical composition which interacts with an active site of MAO B having the sequence SEQ ID No. 1. Furthermore, the pharmaceutical composition may. consist of derivative of FAD, derivatives of acetylenic amine inhibitors, derivatives of cyclopropyl amine inhibitors, derivatives of deprenyl (phenylisopropyl-methylproinylamine) and derivatives of trans-phenylcyclopropylamine. The FAD derivative may include 2'-deoxy FAD or 3'-deoxy FAD.

Furthermore, the present invention is directed to a method of regulating MAO B, comprising the step of mutating an amino acid in the wild type active site shown in SEQ ID No. 1. Specifically, the wild-type amino acid to be mutated may be Phe423, Glu427 or Thr428.

It will be apparent to one skilled in the art that various substitutions and modifications may be made to the invention disclosed herein without departing from the scope and spirit of the invention. The following examples are given for the purpose of illustrating various embodiments of the invention and are not meant to limit the present invention in any fashion:

EXAMPLE 1

Sequence Comparison

Powell et al. (1) determined the amino acid sequence of bovine MAO A and identified a short segment that exhibited high sequence identity to a region in cytochrome P-450 in rat. FIG. 1 shows the same region in human MAO B aligned with other P-450 enzymes, illustrating that all known P-450 enzymes contain this conserved sequence.

EXAMPLE 2

Three-Dimensional Structure

Examination of this conserved sequence in a P-450 enzyme of known structure, P. Putida P-450cam (12), revealed the location of this sequence within its three-dimensional structure. As seen in FIG. 2, the sequence demonstrates helical three-dimensional structure and is located within the active site of P-450cam in close contact to the camphor substrate. Similarly, in the crystal structure of P-450terp (not shown), the conserved sequence is in the active site and in close contact to the terpinol substrate (13). A third P-450 enzyme in which the three-dimensional structure of the active site has been resolved is P-450BM-3 (14). Although P-450BM-3 contains only 16% sequence identity to P-450cam and differs significantly from P-450cam in tertiary structure, redox partner preferences and substrate specificities, the region of high sequence homology in the conserved sequence (shown in FIG. 1) is retained. In these P-450 enzymes, the conserved sequence resides within an extended α-helix which traverses the active site.

To determine whether MAO B could adopt a similar helical structure in the conserved region of interest, secondary structure predictions were carried out using several different methods, including Gibrat, Levin, DPM, PhD and SOPMA (15). All methods predicted the region in MAO B from residues 410–455 to be primarily α-helical. The average of the five methods predicts that the region of MAO B from residues 410–455 is 74% helical.

EXAMPLE 3

Site-Directed Mutagenesis

Site-directed mutagenesis studies have been undertaken in numerous laboratories to identify specific residues that play a role in the active site (16). Although the specific role of several amino acid residues in this region are being investigated, the residues which align with Glu427 and Thr428 in MAO B are widely accepted as crucial for the activity of P-450 enzymes (17).

Figure 3:
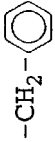
FIG. 3 shows the nucleotide sequences of mutagenic primers used for site-directed mutagenesis studies. Lower-case letters indicate base substitutions. The codons for wild-type and mutants are shown above the nucleotides. Base substitutions which do not alter the amino acid coding sequence were also included in each primer to create a NgoMI restriction site for the purpose of selection. Asterisks indicate codon-retaining mutations which were incorporated to eliminate the formation of a stable hairpin loop in primers during hybridization. Site-directed mutagenesis was carried out by the method of Deng and Nickoloff (26) in a pSVK3 expression vector as previously described (27).

To examine the role of these two amino acid residues in MAO B, point mutations were constructed at positions 427 and 428 within the homologous sequence (FIG. 3). Glu427 was changed to Gln (E427Q), and Thr428 was changed to Ser (T428S) or Ala (T428A), alterations which were consistent with mutagenesis studies carried out with the P-450 enzymes (17). Also, a Phe residue at position 423 was changed to a nonaromatic Ala residue (F423A).

Site-directed mutagenesis was performed by the method of Deng and Nickoloff (26) using a "Transformer Site-Directed Mutagenesis" kit (Clontech) as described previously (27). The mutagenic primers and the corresponding amino acid changes are shown in FIG. 3. All mutagenic primers were designed to create a new restriction site, without altering the coding sequence of any other amino acids, for the purpose of screening.

Construction of mutants was carried out directly within the expression vector pSVK3 with human MAO B cDNA inserted directly into the EcoRI site. Base substitutions which do not alter the amino acid coding sequence were also included in each mutagenic primer to create a NgoMI restriction site for the purpose of selection. The mutant clones were screened for the presence of the new restriction site created by the mutagenic primer. The presence of the correct mutations in all mutant cDNAs were confirmed by double-stranded di-deoxy DNA sequencing (Sanger et al., 1977). Both wild-type and mutant plasmid DNAs were purified through cesium chloride gradients prior to transfection studies.

The wild-type and mutant MAO B enzymes were expressed in mammalian COS-7 cells, and the enzymatic properties of the native enzyme and its mutant enzymes were determined and compared. Wild-type and mutant MAO B cDNAs were transiently transfected into COS-7 cells by electroporation. Cells were harvested during late log phase growth and resuspended to a concentration of $3.125 \times 10^6$ cells/ml in DMEM supplemented with 10% fetal bovine serum (FBS). Fifteen μg of normal or mutant cDNA were added to 0.8 ml ($2.5 \times 10^6$ cells) of cell suspension. Electroporation was carried out in a Bio-Rad Gene Pulser with a setting of 0.25 kV and 500 μF. Cells were resuspended in 15 ml of DMEM/FBS and incubated at 37° C. with 5% $CO_2$ for 48 h.

EXAMPLE 4

Expression Levels of Mutant and Wildtype MAO B: Kinetic Analysis

Expression studies were carried out in mammalian COS-7 cells, since these cells do not contain any detectable endogenous MAO B, as determined by ELISA, Western blot and radiometric activity assays (28). Aliquots (20 μl) of transfected COS-7 cell homogenates were incubated for 10 min at 37° C. in the presence of various concentrations of [$^{14}$C]PEA (20 mCi/mmol) or [$^{14}$C]benzylamine (10 mCi/mmol) in 50 mM sodium phosphate buffer, pH 7.5 (200 μl total volume). Substrate concentrations ranged from 0.25–2.5 times the $K_m$ value (determined in pilot experiments) to yield 10 equally-spaced reciprocal increments. Parallel assays were carried out with untransfected COS-7 cell lysates as a control. Reactions were stopped by addition of 25 μl of 6 N HCl and the deaminated products were extracted by vortexing for 30 seconds with 500 μl of toluene or toluene:ethyl acetate (1:1) for benzylamine or PEA, respectively. Samples were processed as described previously (28). Apparent $K_m$ and $V_{max}$ values were determined by linear regression analysis of Lineweaver-Burk plots. $K_{cat}$ values were calculated from the $V_{max}$ values divided by the concentration of wild-type or mutant MAO B determined in each experiment. Expression levels of wild-type or mutant MAO B were determined in triplicate for six separate experiments as follows: wild-type=11.1+2.07; F423A=9.30+1.89; E427Q=10.3+1.29; T428A=10.2+2.07; T428S=10.2+1.53 pmol MAO B/mg protein. Data are given as means +S.E.M. pmol/mg of protein determined using a subunit molecular weight of 58,800.

Kinetic analysis of the E427Q mutant enzyme showed a profound decrease in activity with either PEA or benzylamine as substrate (Tables 1 and 2), estimated at <5% of wild-type. Since the E427Q mutant replaces an ionizable carboxylate group with an amide group, the loss of activity may be due to an inability of the amide group to participate in a critical ionic bond or proton-dependent step in the reaction. Furthermore, a mutation affecting a proton-dependent step in the reaction would be expected to change the pH profile of the enzyme.

TABLE 1

Apparent kinetic parameters of wild-type and mutant MAO B with PEA substrate

| Enzyme | $K_{cat}$ (min$^{-1}$) | $V_{max}$ (nmol/min · mg protein) | $K_m$ (μM) | $K_{cat}/K_m$ (μM$^{-1}$min$^{-1}$) |
|---|---|---|---|---|
| wild-type | 29.8 + 5.0 | 0.325 + 0.008 | 3.38 + 0.22 | 8.82 |
| F423A | (<5% wt) | — | — | — |
| E427Q | (<5% wt) | — | — | — |
| T428A | 14.3 + 2.6 | 0.161 + 0.039 | 11.1 + 3.7 | 1.29 |
| T428S | 14.5 + 2.0 | 0.162 + 0.22 | 11.6 + 2.3 | 1.25 |

Data are given as means ±S.E.M., where n is equal to three separate experiments. Dashed lines indicate that activity was too low to determine kinetic parameters.

TABLE 2

Apparent kinetic parameters of wild-type and mutant MAO B with benzylamine as substrate

| Enzyme | $K_{cat}$ (min$^{-1}$) | $V_{max}$ (nmol/min · mg protein) | $K_m$ (μM) | $K_{cat}/K_m$ (μM$^{-1}$min$^{-1}$) |
|---|---|---|---|---|
| wild-type | 83.0 + 14.4 | 0.879 + 0.19 | 19.3 + 3.6 | 4.30 |
| F423A | (<5% wt) | — | — | — |
| E427Q | (<5% wt) | — | — | — |
| T428A | 46.2 + 19.1 | 0.374 + 0.06 | 18.6 + 5.6 | 2.48 |
| T428S | 27.2 + 5.8 | 0.236 + 0.05 | 5.4 + 5.4 | 1.77 |

Data are given as means ±S.E.M., where n is equal to three separate experiments. Dashed lines indicate that activity was too low t o determine kinetic parameters.

EXAMPLE 5

Effect of pH on Activity

Figure 4:
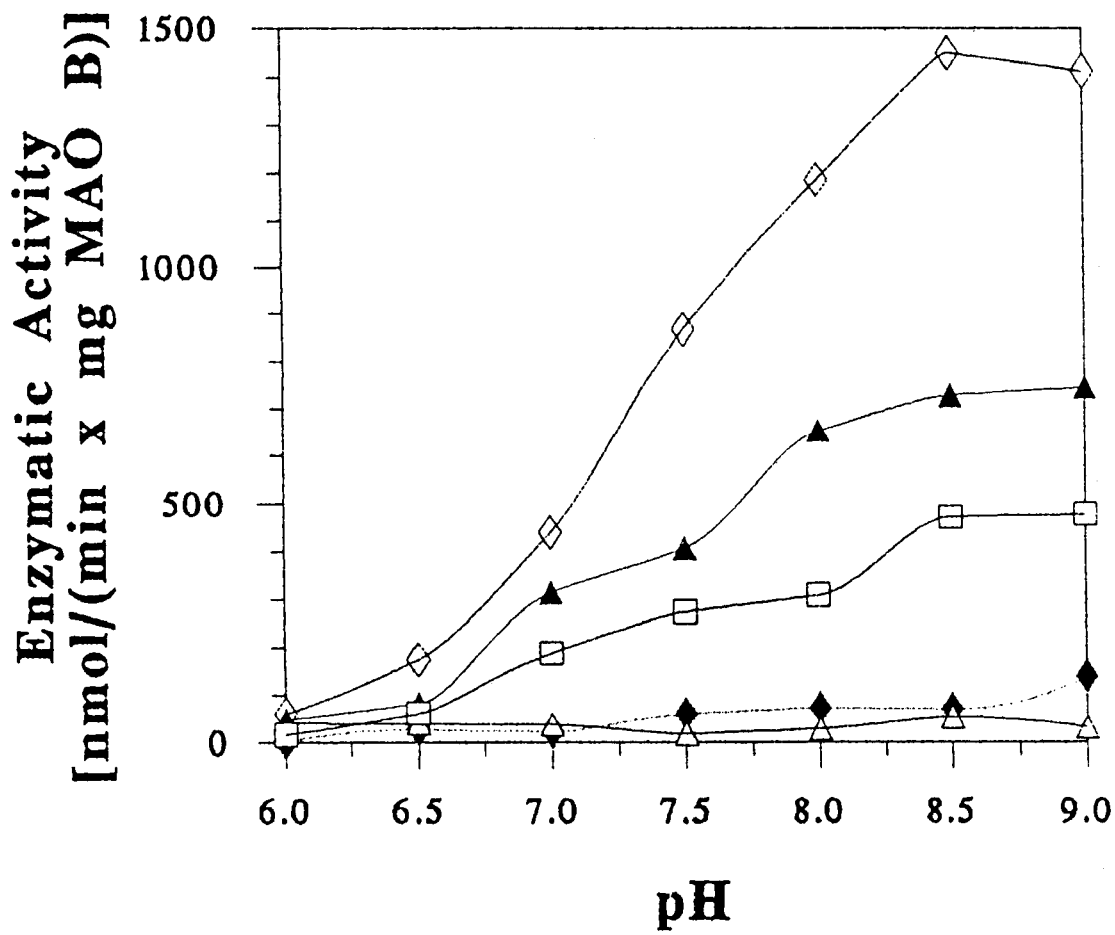
FIG. 4 shows the pH profiles of wild-type and mutant MAO B. Enzymatic activity of wild-type (◇), T428A(△), T428S( ), F423A(◆) and E427Q(▲) was determined for each pH unit. Aliquots (20 μl) of transfected COS-7 cell homogenates were incubated for 10 min at 37° C. in the presence of 500 μM ($^{14}$C)benzylamine (2.5 mCi/mmol) in 50 mM sodium phosphate buffer, pH 6.0, 6.5, 7.0, 7.5, 8.0, 8.5 or 9.0 (200 μl total volume). Reactions were stopped by addition of 25 μl of 6 N HCl. Parallel assays were carried out with untransfected COS-7 homogenates as a control. Samples were processed as previously described (28) and the derived specific activity values (nmol/min-mg protein) were divided by wild-type or mutant MAO B concentration, determined for each experiment, to obtain enzymatic activity values (nmol/min-mg MAO B). Enzymatic activities were determined in duplicate for three separate experiments.

To examine the possibility that the mutation effects a proton-dependent step in the reaction, the enzymatic activity of the mutant and wild-type MAO B enzymes was determined at different pH values from 6.0 to 9.0 (FIG. 4). Although the activity of the E427Q mutant was low (<5% of wild-type), the pH profile appeared significantly different than the wild-type enzyme. The activity of E427Q was essentially independent of pH, whereas the wild-type enzyme displayed a characteristic increase in activity with increasing pH.

The dramatic loss of activity and the change in the pH profile are strikingly similar to results obtained by substitution of the corresponding residue in the P-450 enzymes. For example, mutagenesis of the corresponding residue (Glu or Asp) in P-450cam, P-450d or aromatase also resulted in a dramatic decrease in activities (18). Furthermore, Gerber and Sligar (18) observed a significant change in the pH profile of P-450cam when Asp251 was changed to Asn (from parabolic to descending slope). They proposed a model in which Asp251 and Thr252 of P-450cam provide a proton relay to protonate the heme-bound dioxygen prior to O—O bond scission and water release. A similar mechanism could occur in MAO where Glu427 and Thr428 provide a proton relay to protonate a flavin-bound dioxygen in the reoxidation of FAD. However, while dioxygen is involved in the reoxidation of FADH$^-$, a C(4$\alpha$)-flavin hydroperoxide anion intermediate such as that observed in the flavin monooxygenases (19), has never been observed with the MAO enzymes.

EXAMPLE 6

Criticality of Specific Residues

Several observations indicate that Glu427 in MAO B may play a similar role as the corresponding Asp residue in P-450cam: 1) the region in MAO B contains a high sequence identity to the P-450 enzymes; 2) the region in MAO B is predicted to have a similar secondary structure to the P-450 enzymes ($\alpha$-helix); 3) a Glu or Asp is always observed at this position in MAO B and in the P-450 enzymes; 4) mutagenesis of the residue results in near-complete loss of activity of MAO B, as observed with the P-450 enzymes; and 5) mutagenesis of the residue results in an alteration of the pH profile for MAO B, as observed with the P-450 enzymes.

Substitution of the conserved Thr to Ala (T428A) or to Ser (T428S) in MAO B resulted in similar kinetic profiles. Using PEA as substrate, mutant enzymes showed a shift in the $K_m$ from 3.38 $\mu$M (wild-type) to greater than 11 $\mu$M, and approximately equal reductions (~50% of wild-type) in $K_{cat}$. Using benzylamine as substrate, T428A and T428S showed $K_m$ values approximately equal to wild-type. However, the $K_{cat}$ was reduced by 44% and 67% for T428A and T428S, respectively. This was unexpected, since the Ser side chain contains an hydroxyl group, as does the wild-type Thr. P-450 studies have also reported greater than 50% reduction in activity using a conserved Thr to Ser substitution (24). These results suggest that the hydroxyl side chain must be present in a similar conformation as the wild-type Thr. An hydroxyl group in the wrong conformation may cause a deleterious effect on catalysis by inducing a slight local conformational change, or by steric interference with the binding of substrate or $O_2$.

Another mutant enzyme, F423A, was prepared to examine the role of the upstream aromatic moiety or moieties seen in many of the P-450 enzymes and MAO (see FIG. 1). One or two Phe residues are present in the mammalian enzymes, but are absent in the P-450cam and P-450terp bacterial enzymes. Furuya et al. (18) used site-directed mutagenesis to change Phe313 of P-450d to Tyr, observing a decrease in the $K_{cat}$ of approximately 80% or 25% for benzphetamine or 7-ethoxycoumarin, respectively. This suggests that the Phe is conserved in this location to serve a role in packing, since this side chain extends into a hydrophobic portion of P-450cam near the active site.

In the studies leading to the present invention, the conserved Phe residue was converted to Ala (F423A). It was found that this mutant underwent a dramatic decrease in activity (>95% reduction) compared to the wild-type enzyme, supporting the "protein packing" hypothesis.

The enzymatic activity of F423A was determined over a pH range from 6.0 to 9.0 (FIG. 4). Since the Phe side chain is likely to be involved in protein packing and unlikely to donate a proton in a direct pH dependent reaction, a significant deviation from the wild-type pH profile was unlikely, and, as expected, the pH profile was fairly similar to wild-type MAO B although the activity was largely reduced. Only at pH 9.0 was a significant difference in the shape of the profile observed, where the activity of F423A continued to increase. Thus, the decrease in activity may be attributed to disruption of a critical protein packing region in close proximity to the active site as hypothesized for P-450d.

The following references were cited herein:
1. Human MAO A and B- A. W. J. Bach et al., *Proc. Natl. Acad. Sci.* 85, 4934 (1988); Human MAO B- Y-P. P. Hsu et al., *J. Neurochem.* 51, 1321 (1988); Rat MAO A- T. Kuwahara, S. Takamoto, A. Ito, *Agric. Biol. Chem.* 54, 253 (1990); Rat MAO B- A. Ito, T. Kuwahara, S. Inadome, Y. Sagara, *Biochem. Biophys. Res. Commun.* 157, 970 (1988); Bovine MAO A- J. F. Powell et al., *Biochem. J.* 259, 407 (1989)
2. J. Grimsby, et al., *Proc. Natl. Acad. Sci.* 8, 3637 (1991); Z.-Y. Chen et al., *Nucleic Acid Res.* 19, 4537 (1991); S.-W. Kwan, et al., *Psychopharmacology* 106, 51 (1992).
3. P. L. Dostert, et al., *Med. Res. Rev.* 9, 45 (1989).
4. Westlund, et al., *Science* 230, 181 (1985); Thorpe, et al., *J. Histochem. Cytochem.* 35, 23 (1987); Westlund, et al., *Neurosci.* 25, 439 (1988).
5. R. M. Denney, et al., *Science* 215, 1400 (1982); P. Levitt, J. E. Pintar, X. O. Breakefield, *Proc. Natl. Acad. Sci.* 79, 6385 (1982); R. M. Denney, L. M. Kochersperger et al., *J. Neurosci.* 11, 2874 (1985).
6. Nagy, et al., *Arch. Biochem. Biophys.* 208, 388 (1981); Dostert, et al., *Biochem. Soc. Trans.* 19, 207 (1991); R. B. Silverman *Biochem. Soc. Trans.* 19, 201 (1991); Efange, et al., *J. Med. Chem.* 36, 1278 (1993).
7. B. H. Nicholson *Biochem. Soc. Trans.* 19, 24s (1991).
8. Wouters et al., *Biochem. Biophys. Res. Commun.* 208, 773 (1995).
9. H.-F. Wu, K. Chen, J. C. Shih *Mol. Pharmacol.* 43, 888 (1993); J. Gottowik, A. M. Cesura, P. Malherbe, G. Lang, M. Da Prada, *FEBS Lett.* 317, 152 (1993); S.-W. Kwan, et al., *Archs. Biochem. Biophys.* 316, 385 (1995); B. P. Zhou, D. A. Lewis, et al., *J. Biol. Chem.* 270, 23653 (1995); B. P. Zhou, D. et al., *Biochemistry* 34, 9526 (1995).
10. J. Gottowik, et al., *FEBS Lett.* 317, 152 (1993); F. Ogata, et al., in *Flavins and Flavoproteins* (Walter de Gruyter & Co., Berlin N.Y.), pp. 795–798; J. Gottowik, et al., *Eur. J. Biochem.* 230, 934 (1995).
11. J. Mitoma, A. Ito, *J. Biochem.* (Tokyo) 111, 20 (1992); W. Weyler, *J Neural Transm.* (Suppl) 41, 3 (1994).

12. T. L. Poulos, et al., *J. Biol. Chem.* 260, 16122 (1985); T. L. Poulos, B. C. Finzel, A. J. Howard, *J. Mol. Biol.* 195, 687 (1987)
13. C. A. Hasemann, K. G. Ravichandran, J. A. Peterson, J. Deisenhofer, *J. Mol. Biol.* 236, 1169 (1994).
14. K. G. Ravichandran, et al., *Science* 261, 731 (1993).
15. Gibrat Method- J. F. Gibrat et al., *J. Mol. Biol.* 198, 425 (1987); Levin Method- J. M. Levin, et al., *FEBS Lett.* 205, 303 (1986); DPM Method- G. Deleage, B. Roux, *Protein Engineering* 1, 289 (1987); PhD Method- B. Rost, C. Sander, Proteins 19, 55 (1994);
16. T. Omura, Y. Ishimura, Y. Fujii-Kuriyama, in *Cytochrome P-450*, T. Omura, et al., Eds., (VCH Publishers Inc., N.Y., 1993) p. 23.
17. H. Furuya, T. Shimizu, K. Hirano, M. Hatano, Y. Fujii-Kuriyama, *Biochemistry* 28, 6848 (1989); N. C. Gerber, S. Sligar, *J. Biol. Chem.* 269, 4260 (1994).
18. N. C. Gerber, S. Sligar, *J. Biol. Chem.* 269, 4260 (1994); N. C. Gerber, S. G. Sligar, *J. Am. Chem. Soc.* 114, 8742 (1992); M. Ishigooka, T. Shimizu, K. Hiroya, M. Hatano, *Biochemistry* 31, 1528 (1992); H. Shimada, R. Makino, M. Imai, T. Horiuchi, Y. Ishimura, Mechanism of Oxygen Activation by Cytochrome P-450cam, *International Symposium on Oxygenases and Oxygen Activation*, 1990; D. Zhou, K R. Korzekwa, T. Poulos, S. Chen, *J. Biol. Chem.* 267, 762 (1992); H. Furuya, et al., *Biochemistry* 28, 6848 (1989).
19. D. P. Ballou, in *Flavins and Flavoproteins*, R. C. Bray, P. C Engel and S. G. Mayhew, Eds. (Walter de Gruyter, Berlin N.Y., 1984) pp. 605–618.
20. E. Deprez et al., *Biochemistry* 33, 14464 (1994).
21. T. L. Poulos, B. C. Finzel, J. J. Howard, *J. Mol. Biol.* 195, 687 (1987); R. Raag, T. L. Poulos, *Biochemistry* 28, 7586 (1989).
22. R. Raag, S. A. Martinis, S. G. Sligar, T. L. Poulos, *Biochemistry* 30, 11420 (1991).
23. Y. Imai, M. Nakumura, *FEBS Lett.* 234, 313 (1988); Y. Imai, M. Nakamura, *Biochem. Biophys. Res. Commun.* 158, 717 (1989); N. Hanoika et al., *Biochemistry* 31, 3364 (1992); T. Fukuda et al., *J. Biochem.* (Tokyo) 113, 7 (1993).
24. S. Chen, D. Zhou, *J. Biol. Chem.* 267, 22587 (1992); Y. He, et al., *Biochemistry* 33, 419 (1994).
25. D. R. Nelson, H. W. Strobel, *Biochemistry* 28, 656 (1988).
26. W. P. Deng, J. A. Nickoloff, *Anal. Biochem.* 200, 81 (1992).
27. B. P. Zhou, et al., *Biochemistry* 34, 9526 (1995).
28. Kwan, et al., *Archs. Biochem. Biophys.* 316, 385 (1995)

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated, mutated MAO B enzyme having at least one amino acid substitution for wildtype amino acids in a MAO B active site, wherein said wildtype amino acid is selected from the group of Phe423, Glu427 and Thr428.

2. An isolated DNA encoding the isolated, mutated MAO B enzyme of claim 1.

3. A plasmid containing said DNA of claim 2 and regulatory elements necessary for expression of said DNA in a cell.

4. The isolated, genetically-engineered cellular MAO B enzyme of claim 1, wherein alanine is substituted for Phe423 of the wildtype enzyme.

* * * * *

UNITED STATES PATENT AND TRADEMARK OFFICE
CERTIFICATE OF CORRECTION

PATENT NO. : 6,451,570 B1
DATED : September 17, 2002
INVENTOR(S) : Creed W. Abell and Duane A. Lewis It is certified that error appears in the above-identified patent and that said Letters Patent is hereby corrected as shown below:

Column 1,
Line 7, "1,998" should read -- 1998 --.
Line 28, "a n" should read -- an --.

Column 2,
Line 4, "wild-type" should read -- wildtype --.
Line 27, "i n" should read -- in --.

Column 3,
Line 61, please delete the comma after "be".

Column 4,
Lines 20, 29, 30 and 41, "wild-type" should read -- wildtype --.
Line 55, "SHT" should read -- 5HT --.

Column 5,
Line 23, please delete the comma after "Freshney".

Column 6,
Line 6, "b y" should read -- by --.
Line 60, please remove the indentation before "See, e.g.".

Column 7,
Line 12, "i n" should read -- in --.

Column 8,
Line 13, please delete the period after "may".
Line 22, "wild-type" should read -- wildtype --.
Line 38, please insert the word -- the -- after "P-450 in".

Column 9,
Lines 42 and 46, "wild-type" should read -- wildtype --.
Line 49, "Wild-type" should read -- Wildtype --.

Column 10,
Lines 17, 20 and 28, "wild-type" should read -- wildtype --.
Line 26, "benzy-lamine" should read -- benzyl-amine --.
Lines 37 and 43, in Table 1, "wild-type" should read -- wildtype --.
Lines 49 and 66, "Dashed lines" should read -- Dashes --.
Lines 54 and 59, in Table 2, "wild-type" should read -- wildtype --.

Column 11,
Lines 6, 10, 11, 51, 52, 54 and 57, "wild-type" should read -- wildtype --.
Line 29, "(4α)" should read -- (4α) --.

UNITED STATES PATENT AND TRADEMARK OFFICE
CERTIFICATE OF CORRECTION

PATENT NO. : 6,451,570 B1
DATED : September 17, 2002
INVENTOR(S) : Creed W. Abell and Duane A. Lewis It is certified that error appears in the above-identified patent and that said Letters Patent is hereby corrected as shown below:

<u>Column 11 cont'd,</u>
Line 31, "never-been" should read -- never been --.
Line 57, "an" should read -- a --.
Line 61, "An" should read -- A --.

<u>Column 12,</u>
Lines 14 and 22, "wild-type" should read -- wildtype --.
Lines 29 and 33, "B- A" should read -- B - A --.
Line 30, "B- Y" should read -- B - Y --.
Line 31, "MAO A" should read -- MAO - A --.
Line 35, "A- J" should read -- A - J --.
Line 37, please delete the comma after "Grimsby".
Line 39, please delete the comma after "Kwan".
Line 40, please delete the comma after "Dostert".
Lines 41 and 42, please delete the comma after "Westlund".
Line 41, please delete the comma after "Thorpe".
Line 44, please delete the comma after "Denney".

<u>Column 13,</u>
Line 9, "Method- G." should read -- Method - G. --
Line 10, "Method- B." should read -- Method - B. --
Line 11, "Proteins" should be italicized.
Line 13, please delete the comma after "Omura".
Line 26, please delete the comma after "Furuya".
Line 30, please insert -- & -- between "Berlin" and "N.Y.".

<u>Column 14,</u>
Line 9, please delete the comma after "He".
Line 15, please delete the comma after "Zhou".
Between lines 15 and 16, please insert a line break before the paragraph beginning with "Any patents or publications mentioned".

UNITED STATES PATENT AND TRADEMARK OFFICE
CERTIFICATE OF CORRECTION

PATENT NO.     : 6,451,570 B1
DATED          : September 17, 2002
INVENTOR(S)    : Creed W. Abell and Duane A. Lewis It is certified that error appears in the above-identified patent and that said Letters Patent is hereby corrected as shown below:

<u>Column 14 cont'd,</u>
Line 16, please delete the comma after "Kwan".

Signed and Sealed this

Twenty-sixth Day of August, 2003

JAMES E. ROGAN
*Director of the United States Patent and Trademark Office*